United States Patent [19]

Stein

[11] 4,379,459
[45] Apr. 12, 1983

[54] CARDIAC PACEMAKER SENSE AMPLIFIER

[75] Inventor: Marc T. Stein, Tempe, Ariz.

[73] Assignee: Medtronic, Inc., Minneapolis, Minn.

[21] Appl. No.: 252,537

[22] Filed: Apr. 9, 1981

[51] Int. Cl.³ .............................................. A61N 1/36
[52] U.S. Cl. ............................................. 128/419 PG
[58] Field of Search ................... 128/419 PT, 419 PG,
128/708, 901

[56] References Cited

U.S. PATENT DOCUMENTS

| | | | |
|---|---|---|---|
| 3,678,937 | 7/1972 | Cole et al. ...................... | 128/419 PG |
| 3,718,909 | 2/1973 | Greatbatch .................... | 128/419 PT |
| 3,927,677 | 12/1975 | Gobeli et al. ................. | 128/419 PG |
| 4,114,627 | 9/1978 | Lewyn et al. ................. | 128/419 PT |
| 4,266,551 | 5/1981 | Stein .............................. | 128/419 PG |

Primary Examiner—Kyle L. Howell
Assistant Examiner—Mitchell J. Shein
Attorney, Agent, or Firm—Joseph F. Breimayer; Robert C. Beck; John L. Rooney

[57] ABSTRACT

A demand cardiac pacemaker of the type having sense amplifier circuitry for detecting the occurrence of natural heart activity which establishes a first level representative of sensed extraneous repetitive noise and a second level greater in absolute value than the reference by an amount representative of sensed heart activity. Circuitry differentially responsive to the difference between the reference and second level detects the occurrence of natural heart activity. The sense amplifier circuitry is blanked, that is disconnected from the terminals coupled to the heart, for a blanking interval following stimulation to avoid saturation of the sense amplifier stages and the erroneous detection of a pacing stimulus. Any reference level voltages developed by extraneous repetitive noise are retained during blanking to prevent the differential circuitry from interpreting the noise signal sensed at the end of the blanking interval as a heart signal. The amount by which the reference and second level must differ to indicate natural heart activity is established by a bias circuit, the bias being alterable to establish one of a preselected plurality of sensitivities.

3 Claims, 3 Drawing Figures

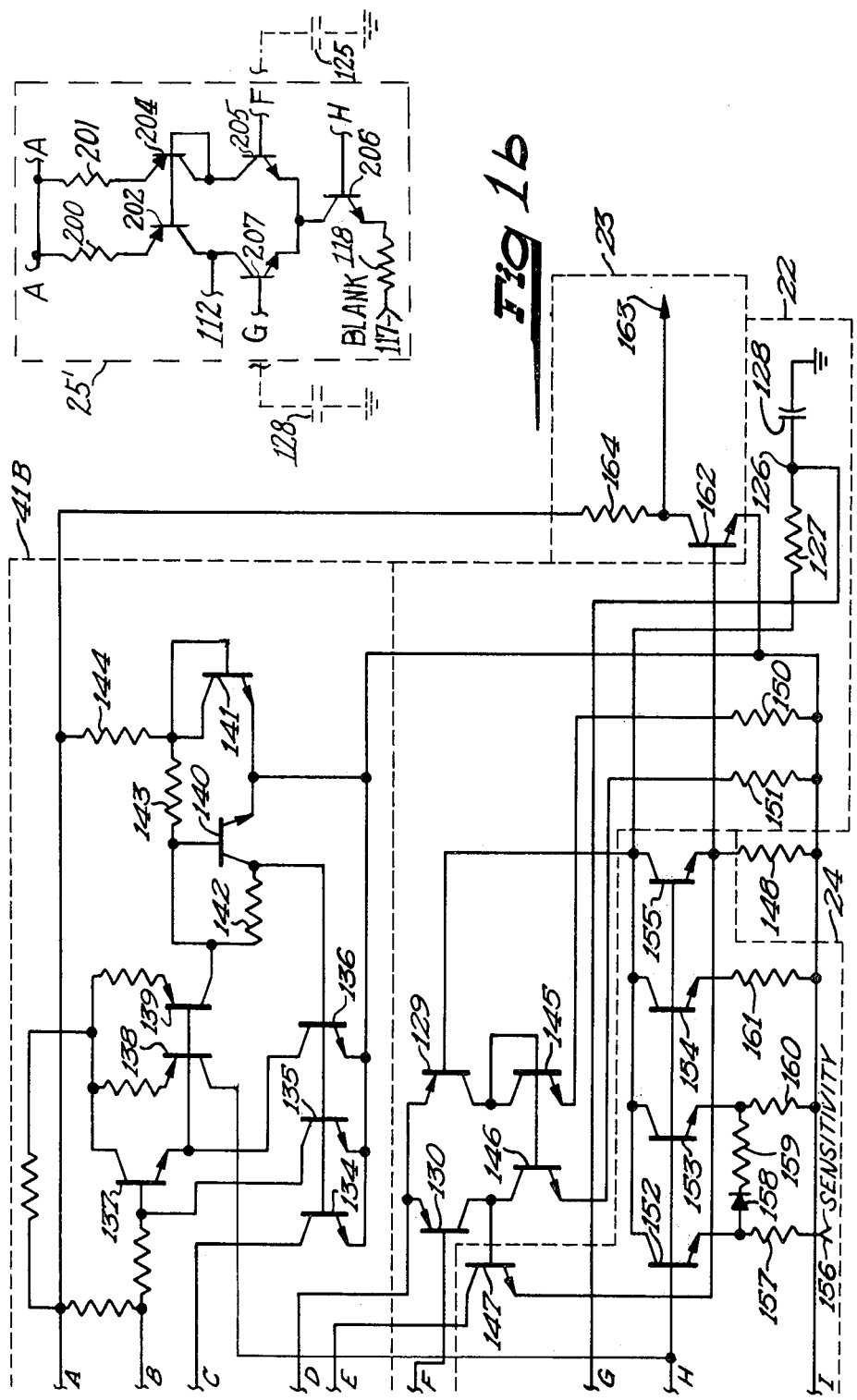

CARDIAC PACEMAKER SENSE AMPLIFIER

BACKGROUND OF THE INVENTION

1. Field of the Invention

The present invention relates generally to a cardiac pacemaker sense amplifier that discriminates between actual heart signals and extraneous repetitive noise signals.

2. Description of the Prior Art

Demand cardiac pacemakers are well known to those familiar with the art. Such pacemakers provide a heart stimulating pulse to the patient's heart only in the absence of an actual heartbeat and are inhibited should the natural heartbeat recur at a rate exceeding a preset demand pacing rate. Such pacemakers are commonly of the ventricular inhibited type which are designed to sense a QRS complex within the escape interval programmed for its basic rate and to recycle without producing a ventricular stimulating pulse but may take the form of an atrial inhibited pulse generator, atrial synchronous, ventricular inhibited pulse generator, atrial or ventricular synchronous triggered pulse generator, or atrial-ventricular sequential pulse generator. Such pacemakers are described in the article entitled "The Report of Inter-Society Commision for Heart Diseases Resources, Implantable Cardiac Pacemakers Status Report and Resource Guideline" published by the magazine Circulation, Vol. L, October 1974. A further, more recent pacemaker, employs both atrial and ventricular sense amplifiers and pulse generators and operates in a fully automatic mode, as described in co-pending U.S. patent application Ser. No. 235,069, filed Feb. 17, 1981, in the name of L. Herpers and assigned to assignee of the present invention. Such an automatic pacemaker possesses timing circuitry for providing atrial and ventricular escape intervals and the A-V timing interval and coupling circuitry which causes the timing circuitry to be reset upon sensing either an atrial heart depolarization, or P wave, or a ventricular heart depolarization, or R wave. The amplitude and frequency components of the P wave and the R wave differ from one another and the atrial and ventricular sense amplifiers must accordingly be designed to respond to the particular heart signal. To complicate matters, the P and R waves may be detected in either chamber and retrograde R-waves may mimic P-waves in the atrium.

In practice, it has been found that other signals generally referred to as electro-magnetic interference or EMI may possess frequency components, amplitudes and slew rates which can likewise be interpreted as a natural heart signal. For example, strong electrical signals commonly encountered in the environment, such as stray 60 Hz energy, may result in the inhibiting of the stimulating pulse as if a natural heartbeat had not been detected. To prevent the inhibiting of a stimulating pulse by extraneous noise, typical prior art demand cardiac pacemakers have been provided with noise rejection circuitry, shielding, or reversion circuitry to convert the operation of the pacemaker into a fixed rate or asynchronous mode of operation.

In the U.S. Pat. No. 3,927,677 assigned to the assignee of the present invention, a reversion circuit is described which is capable of detecting actual heart activity in the presence of extraneous repetitive noise. That circuit has proven to substantially alleviate the effects of EMI and to allow the pacemaker to discriminate between actual heart signals and the background repetitive noise.

However, the application of the reversion circuitry of U.S. Pat. No. 3,927,677 to atrial and ventricular pacemakers causes special problems arising from the fact that the atrial or ventricular sense amplifiers must be blanked or disconnected for blanking intervals commencing on the production of a respective ventricular or atrial pacing stimulus to prevent that stimulus from being detected as a natural heart depolarization and from overloading the sense amplifier input stages. The disconnection and subsequent reconnection of the input stages of the sense amplifier presents a special problem to the reversion circuitry found useful in the discrimination between electromagnetic interference and natural heart signals. The initial noise impulse upon reconnection could be mistakenly interpreted as a natural heart depolarization.

SUMMARY OF THE INVENTION

The present invention provides a reversion circuit which discriminates between natural heart activity and extraneous repetitive noise or electromagnetic interference even though the circuit is periodically disconnected from the source of the electromagnetic interference. The circuitry performing this function will also reject nonrepetitive signals whose amplitude is below predetermined values. According to the present invention, the reconnection of the sense amplifier to the output terminals of the pulse generator and the application of noise thereon to the reversion stages of the sense amplifier will not cause the sense amplifier to interpret the initial transition of the noise signal as an actual heart signal.

In accordance with a preferred embodiment of the present invention, the reversion circuit comprises a reference level integrating circuit having a first time constant which establishes a reference level representative of sense extraneous repetitive noise, an instantaneous level integrating circuit having a further shorter time constant, and a differential amplifier which responds to the difference between the amplitudes of the signals on the reference level and instantaneous level integrating circuits.

In the case where continuous EMI, e.g., 60 Hz noise is present and in the absence of cardiac activity, the differential amplifier stage does not provide an output signal since the noise signals are integrated equally over the long time constant reference level integrating circuit and the short time constant instantaneous level integrating circuit. However, when a R wave or P wave is applied to the circuit, the integrator with the short time constant integrates the charge presented to it rapidly and develops a higher voltage than is developed by the long time constant integrator resulting in a differential voltage at the input terminal of the differential amplifier and a resulting output signal.

The termination of the continuous noise level at blanking causes the relatively equal voltage levels on the two integrating circuits to discharge at rates dependent on the respective time constants. At the end of blanking the continuous noise signal is suddenly reapplied to the integrating circuits. The initial incoming transition will likewise be integrated more rapidly by the instantaneous level integrator than by the reference level integrator, resulting in an output signal generated by the differential circuit. In accordance with the present invention, the interruption of the application of the continuous noise signal to the sense amplifier due to the disconnection or blanking thereof is compensated for by comparator circuit means for equalizing and maintaining the levels of the reference level integrator and the instantaneous level integrator relatively equal over the blanking interval.

The further differential amplifier or comparator circuit is interconnected with a Buffer Circuit which provides the current to the reference and instantaneous level integrating circuits. When blanking of the amplifier takes place, the comparator circuit maintains the voltage on the instantaneous level integrating circuit near the previously attained reference level integrating circuit voltage by functioning as a source of current to maintain the voltage or as a current sink to dissipate the voltage which may be imposed by an extraneous signal developed during the blanking interval.

For example, if the circuit to be described is employed as an atrial sense amplifier in the commonly assigned U.S. patent application Ser. No. 235,069 filed on Feb. 17, 1981, then during its blanking, it is not physically disconnected from the atrial pacing and sensing terminals. Consequently, while the output of the circuit may be ignored by or disconnected from the control circuitry, the atrial sense amplifier may be subject to large signals that should be ignored during blanking but may be sensed and amplified and tend to create a voltage signal on the instantaneous level integrating circuit. According to this invention, during blanking such a signal would be dissipated, leaving the voltage levels on the two integrating circuits near their previously achieved levels.

Similarly, if the sense amplifier circuit is employed as a ventricular sense amplifier in the pulse generator circuit of the aforementioned U.S. Ser. No. 235,069, then initially during its blanking interval, the input terminals of the sense amplifier are disconnected. No input signal can reach the two integrating circuits and the problem is to maintain the voltage levels realtively the same as they were when blanking commenced. In this case, the comparator circuit acts as a current source to help maintain the voltage levels near their prior levels during blanking. After the input terminals are reconnected and during the remaining period of the blanking interval, the ventricular sense amplifier is subject to the same problem encountered during blanking of the atrial sense amplifier.

In either case, in the absence of any large input signal the two integrating circuits do not discharge appreciably due to the high resistance of the discharge path and the operation of the comparator circuit.

BRIEF DESCRIPTION OF THE DRAWINGS

Many of the attendant advantages of this invention will be readily appreciated as the same becomes better understood by reference to the following detailed description when considered in connection with the accompanying drawings in which like reference numerals designate like parts throughout the figures thereof and wherein:

FIG. 1A and 1B together comprise the prior art sense amplifier circuit; and

FIG. 2 depicts the blanking circuit components coupled to predetermined points in the circuitry of FIGS. 1A and 1B which constitute the improved sense amplifier of the present invention.

DESCRIPTION OF THE PREFERRED EMBODIMENT

Figure 1A:
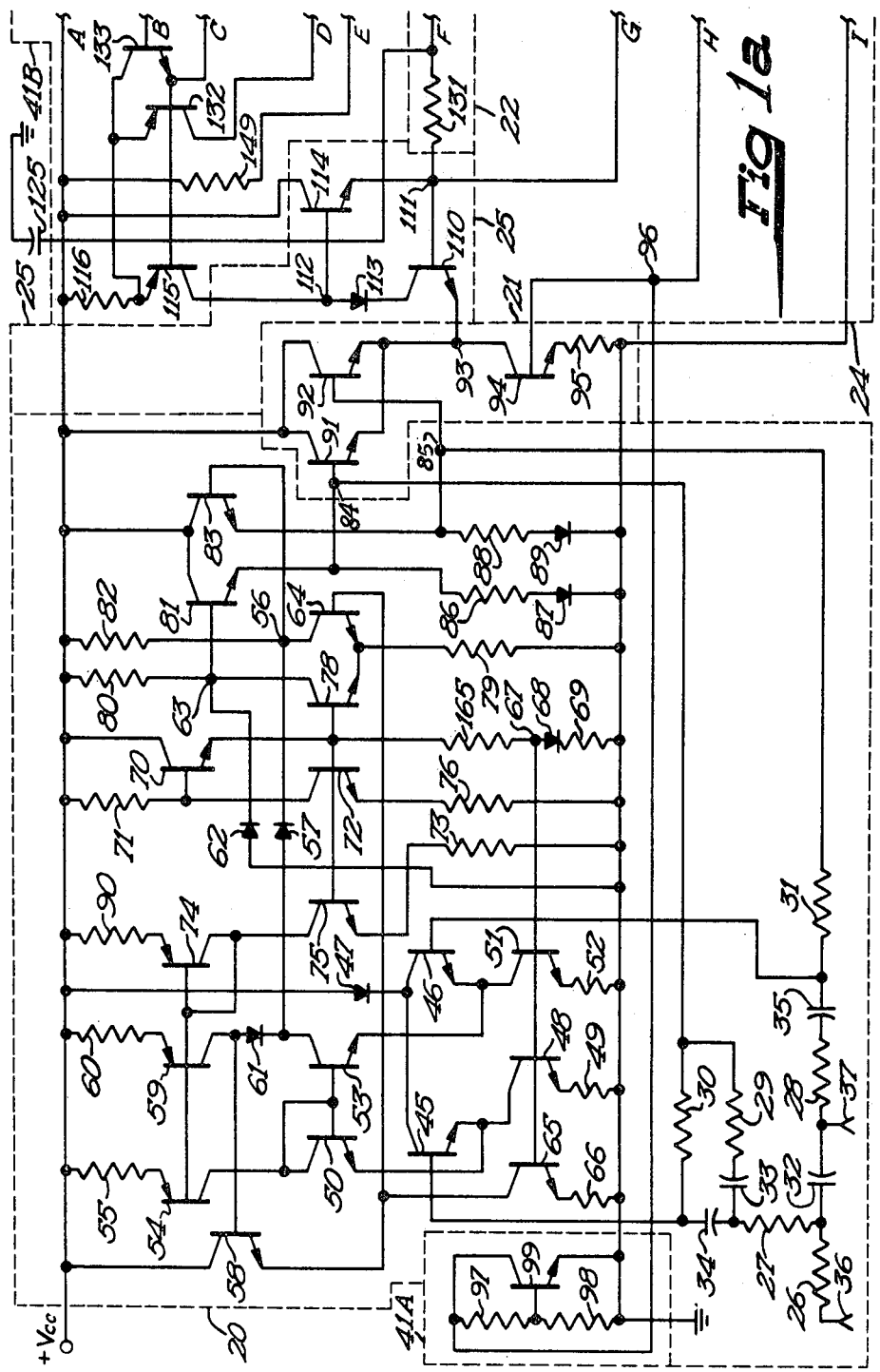

Referring now to FIG. 1 there is illustrated in separate FIGS. 1A and 1B a preferred embodiment of the Sense Amplifier of the present invention with functional elements 20-25 being set out in boxes formed of broken lines. The Sense Amplifier includes a preamplifier section indicated generally at 20, an Absolute Value Circuit 21, a Reversion Circuit 22, an Output Circuit 23 and a Sensitivity Control 24. A Buffer 25 is provided intermediate the Absolute Value Circuit 21 and Reversion Circuit 22 to prevent loading on the Absolute Value circuit from the Reversion Circuit. Buffer 25 is coupled to a blanking circuit of FIG. 2 and is responsive to a BLANK signal (shown in FIG. 2) to turn off and block signals from the Reversion Circuit 22. The BLANK signal can be developed, for example, by digital control and timing circuitry of the type shown for example in U.S. Pat. No. 4,266,551. Alternatively, the BLANK signal can be developed by similar circuitry designed specifically for the blanking of the atrial sense amplifier of an atrial and ventricular demand pacemaker.

Preamplifier 20 is a differential input, differential output device having a dual feedback active filter formed of resistors 26-31 and capacitors 32-35. It is designed to have an open loop gain of approximately 60,000 with a unity gain crossover point of approximately 2 kHz. The dual negative feedback method minimizes the number of external components used. As will be described more fully below, the differential input of the preamplifier 20 allows an essentially polarity independent degree of response to signals appearing at the input terminals 36 and 37. That is, preamplifier 20 is essentially identically responsive to signals appearing at the terminals 36 and 37 without regard to polarity. The differential output of preamplifier 20 provides two signals of opposite polarity but of essentially the same absolute value, each being representative of signals appearing at the inputs 36 and 37.

The Absolute Value Circuit 21 responds to the differential output signals of preamplifier 20 to provide a single polarity signal representative of the signal sensed at the inputs 36 and 37. Thus, preamplifier 20 and Absolute Value Circuit 21 combine to provide signals of a single polarity representative of signals appearing at the terminals 36 and 37, but without regard to the polarity of the signals at the terminals 36 and 37. In this way, the detecting circuitry contained within Reversion Circuit 22 need be responsive to signals of but a single polarity without thereby creating a polarity disparity within the Sense Amplifier. The sensitivity of the Reversion Circuit 22 to the output of the Absolute Value Circuit 21 is controlled by Sensitivity Control 24, the sensitivity being established by the SENSITIVITY signal from the Digital Circuitry of the incorporated U.S. Ser. No. 957,825 causing its timing cycle to be restarted in a known manner. The line between Output Circuit 23 and Sensitivity Control 24 represents a sensitivity hysteresis function which will be explained more fully below.

Boxes 41A and 41B contain elements which set up supply-independent voltage reference and bias currents as is described more fully below. Connecting lines A thru I in FIG. 1A are intended for connection to the line of like reference character on FIG. 1B and FIG. 2.

Signals appearing at the input terminals 36 and 37 are applied through the active filter, to the bases of transistors 45 and 46. Transistors 45 and 46 form the input differential pair having their collectors connected to +Vcc through diode 47. The emitter of transistor 45 is connected to a current sink formed of transistor 48 and resistor 49 and to the emitter of a transistor 50. Similarly, the emitter of transistor 46 is connected to a current sink formed of transistor 51 and resistor 52 and to the emitter of transistor 53. The bases of transistors 50 and 53, and the collector of transistor 50 are connected to a current source formed of transistor 54 and 55. The collector of transistor 53 is connected to a junction 56 via capacitor 57 and, via a diode 61, to the base of transistor 59 and resistor 60. A capacitor 62 connects a junction 63 to ground.

The emitter of transistor 58 is connected to the base of a transistor 64 and to a current sink formed of transistor 65 and resistor 66. The bases of transistors 48, 51 and 65 are connected to a junction 67, the junction 67 being connected to ground via diode 68 and resistor 69 and to a junction 77 via resistor 165. A transistor 70 has its emitter connected to the junction 77, its collector connected to +Vcc while its base is connected to +Vcc via resistor 71 and to the collector of a transistor 72. The emitter of transistor 72 is connected to ground via resistor 76. The base of transistor 59 is connected to the base of transistor 54, the collector and base of a transistor 74 and the collector of a transistor 75. The emitter of transistor 75 is connected to ground via a resistor 73 and the bases of transistor 75, 72 and 78 are commonly connected and are in time connected to the junction 67 via resistor 165. Transistor 78 has its emitter connected to the emitter of transistor 64 and to ground via resistor 79. The collectors of transistors 64 and 78 are connected to junctions 56 and 63, respectively. Junction 63 is connected to +Vcc via resistor 80 and to the base of a transistor 81. Similarly, junction 56 is connected to +Vcc via resistor 82 and to the base of a transistor 83. The collectors of transistors 81 and 83 are connected to +Vcc while their emitters are connected to junctions 84 and 85, respectively. Junctions 84 and 85 serve as the output terminals for preamplifier 20 with junction 84 being connected to ground via resistor 86 and diode 87 and junction 85 being connected to ground via resistor 88 and diode 89.

As stated above, transistors 45 and 46 constitute the input differential pair. Diode 47 prevents base collector current to +Vcc in transistor 46 during a stimulation pulse while diode 61 increases the dynamic range of the input differential pair during supply voltage depletion. Transistors 70 and 72, in conjunction with resistors 71 and 75, set up a +Vcc/2 stable reference at between the junction. Diode 68 and resistors 69 and 165 set up a tail current for transistors 45 and 46 via the current sinks formed in part by transistors 48 and 51 as well as for transistor 58 via the current sink formed in part by transistor 65.

Transistor 58 is an emitter follower which couples the signal from the input differential pair to the transistors 64 and 78 which form the second gain stage in the amplifier. The signals appearing at the junctions 56 and 63 are of opposite polarity having an absolute amplitude value representative of signals appearing across the terminals 36 and 37. The transistors 81 and 83 are emitter followers which drive the Absolute Value Circuit 21. The source current for the input differential pair are set up by transistors 54, 57, 74 and 75 and resistors 55, 60, 76 and 90. Capacitors 57 and 62 set the high frequency rolloff of the preamplifier while diode 87 and resistor 86 and diode 89 and resistor 88 set upon a tail current from the emitter followers formed of transistors 81 and 83, respectively.

Preamplifier 20 has a degree of response essentially independent of the polarity of the signals appearing at the terminals 36 and 37. It has a differential input and a differential output, the signals appearing at the output being of opposite polarity with the absolute value of the signals appearing at the terminals 36 and 37. In this manner, the polarity disparity attending prior art sense amplifiers is greatly reduced and the Sense Amplifier can reliably respond to sensed signals representative of heart activity of either polarity.

The junction 63 is connected to the base of transistor 91 through the base-emitter path of transistor 81 while the junction 56 is connected to the base of transistor 92 through the base-emitter path of transistor 83. The bases of transistors 91 and 92 are also connected to resistors 30 and 31, respectively, resistors 30 and 31 being the negative feedback resistors associated with the active filter. The collectors of transistors 91 and 92 are connected to +Vcc while their emitters are connected to a junction 93. The junction 93 comprises the output terminal of the Absolute Value Circuit 21 and is connected to the collector of a transistor 94. The emitter of transistor 94 is connected to ground via resistor 95 and its base is connected to a junction 96. Resistors 97 and 98 and transistor 99 in box 41A set up a reference voltage which is applied to the base of transistor 94 as well as to transistors forming a portion of the Sensitivity Control 24, as will be described below.

Transistors 91 and 92 are emitter followers. Accordingly, the signal appearing at the junction 93 will approximate the most positive signal appearing at the bases of transistors 91 and 92. Inasmuch as the signals appearing at the junctions 84 and 85 are of opposite polarity, the positive one of those signals will result in a positive signal at the junction 93. Accordingly, a positive signal appears at the junction 93 which is representative of signals appearing at the terminals 36 and 37 without regard to polarity. That is, signals of either polarity appearing at terminals 36 and 37 will result in a single polarity signal (in this case positive) at junction 93, that signal being representative of the signal at the terminals 36 and 37.

With no significant signal at the inputs 36, 37 the voltages are relatively equal as established by transistor 81, 83 and resistors 86, 88. Ordinarily then, the voltage at junctions 84, 85 may be roughly +Vcc/2. The voltage at junction 83 is thus ordinarily +Vcc/2 less the base emitter voltage drop of transistors 91 and 92.

Transistor 94, resistor 95, circuit 41A and transistor 138 (FIG. 1b) establish with transistor 115 and resistor 116 a constant current sink through transistor 94 and resistor 95 to ground. That constant current is twice the current drawn through transistor 110, requiring then that half the current be drawn through the transistors 91 and 92.

Due to the base-emitter drop of transistor 110, junction 111 is ordinarily at the same quiescent voltage level as the junctions 84, 85. Junction 111 serves as the input to Reversion Circuit 22 which includes the instantaneous and reference level integrating circuits (capacitors 128 and 125 respectively) and the differential circuit (transistors 129, 130, 145, 146, and resistors 150, 151).

When a signal at junctions 84, 85 causes transistors 91 or 92 to conduct a greater proportion of the current through transistor 94, the transistor 110 is rendered less conductive causing transistor 114 to become more conductive, and the instantaneous signal voltage at junction 111 follows the change in the instantaneous signal voltage at junction 93, but only after certain voltage rise in the instantaneous signal voltage at junction 93 is achieved.

The signal appearing at junction 111 is applied to a junction 126 between the resistor 127 and a capacitor 128. Capacitor 128 is connected to ground while resistor 127 is connected to the base of a transistor 130 and to capacitor 125 via resistor 131. Capacitor 125 is similarly connected to ground.

The emitters of transistors 129 and 130 are connected to the collector of a transistor 132. Transistor 115 and transistors 132–141, together with their associated resistors within box 41B, set up a supply-independent voltage reference for a Battery Monitor Circuit (not shown) and set bias currents for the unity gain Buffer 25 and Reversion Circuit 22. For example, transistors 134–136 are 2.72 area scaled transistors which, in conjunction with transistor 140 and a resistor 142 set up current in their respective collectors. Transistor 141 together with resistors 143 and 144 provide a current for startup when power is first applied. Transistors 133 and 137 minimize effects on currents at low battery conditions.

The collector of transistor 129 is connected to the collector and base of a transistor 145 (which functions as an active diode) while the collector of transistor 130 is connected to the collector of a transistor 146 and to the base of a transistor 147. The emitter of transistor 147 is connected to ground via resistor 148 and to the base of a transistor 162 while its collector is connected to +Vcc via resistor 149. Transistors 145 and 146 form current sinks in conjunction with resistors 150 and 151, respectively.

Transistor 147 and resistors 148 and 149 provide a sensitivity hysteresis function in a manner to be described more fully below. In addition, Reversion Circuit 22 works in conjunction with Sensitivity Control Circuit 24 and the Output Circuit 23. Transistors 152–155 of Sensitivity Control Circuit 24 have their collectors connected to the base of transistor 129 and their bases connected to junction 96. The emitter of transistor 152 is connected to a terminal 156 via resistor 157 and to the emitter of transistor 153 via diode 158 and resistor 159. The terminal 156 receives the SENSITIVITY signal from the digital circuit of the incorporated specification. The emitter of transistor 153 is connected to ground via resistor 160 while a resistor 161 connects the emitter of transistor 154 to ground. The emitter of transistor 155 is connected to resistor 148, to the emitter of transistor 147 and to the base of transistor 162. Transistor 162 controls the output signal and has its collector connected to a terminal 163 and to +Vcc via resistor 164 while its emitter is connected to ground.

As will become apparent from the following discussion, when no signal is applied to terminal 156, an intermediate sensitivity is selected for the Reversion Circuit 22. When the terminal 156 is connected to a positive potential via the digitial circuitry 10, the Reversion Circuit 22 is in its most sensitive state. Conversely, when the terminal 156 is connected to ground via (for example) the digitial circuitry of the incorporated specification, Reversion Circuit 22 is in its least sensitive state. Assuming for the moment, that Sensitivity Control Circuit 24 is in the intermediate setting (i.e., no signal appearing at terminal 156), each of the current sinks including transistors 153–155 are operative and establish a voltage drop across resistor 127 resulting in the higher conduction of transistor 129 than transistor 130. In this quiescent Reversion Circuit condition, the current through transistor 129 causes transistor 147 to conduct more heavily than transistor 146. But transistor 146 is capable of conducting any current flowing through transistor 130. When a signal is applied to the junction 111, the base of transistor 129 rises more rapidly than the base of transistor 130 because of the time constant associated with resistor 131 and capacitor 125 exceeds that of the the capacitor 128. If the input is of sufficient amplitude to decrease the current drawn from the bases of transistor 129, transistors 129, 145 and 146 become less conductive. Thus transistor 129 becomes less conductive causing the current sinks 145, 146 to become less conductive, while transistor 130 becomes more conductive. When the voltage at the base transistor 129 rises to less than one base-emitter voltage drop of the voltage at the base of transistor 130, transistor 146 is no longer conductive enough to sink the collector current of transistor 130. The resulting increased voltage at the base of transistor 147 renders it and transistor 162 conductive. The turn-on of transistor 162 results in a signal at terminal 163 of ground potential indicating the detection of heart activity.

When the terminal 156 is connected to a positive potential, the current associated with the current sink including transistor 153 is disabled and thus a lesser current is flowing through resistor 127 establishing less of a bias on the base of transistor 129. Thus, Reversion Circuit 22 has a greater sensitivity. Conversely, when terminal 156 is connected to ground, the current sink including transistor 152 is enabled increasing the current flow through resistor 127 and the bias on transistor 129. In this condition, the Reversion Circuit 22 is in its least sensitive setting.

Transistor 147 and resistors 148 and 149 perform a sensitivity hysteresis function to enhance and provision of an output signal. As an output pulse is initiated, the junction between the emitter of transistor 147 and resistor 148 rises in voltage which turns off transistor 155. This decreases the current flow through the resistor 127. Thus, a positive feedback is initiated in that as transistor 129 is turned off by a positive signal coming from the unity gain Buffer 25, an output is initiated and the current through the resistor 127 is lowered resulting in an increase in the base voltage of transistor 129 turning it off even faster. When the output transistor 162 begins to turn off, the voltage at the junction of the emitter of transistor 147 and resistor 148 drops toward ground initiating the flow of current through transistor 155 and increasing the current flow through resistor 127 speeding up the turn on of transistor 129 and, thus, the turnoff of transistor 130.

The essentially polarity independent response of the preamplifier 20 and Absolute Value Circuit 21 for the purpose of reducing polarity disparity are enhanced by the fact that the current sources and sinks have their emitter "degenerated" by resistors which stabilizes them to make them more nearly matching for polarity disparity. However, other techniques may be employed without departing from the scope of the invention. In addition, at least the input differential pair formed of transistors 45 and 46 and the Absolute Value Circuit transistors 91 and 92 are preferably "matched" by placing them in close proximity and providing them with the same geometry and connections, again for polarity disparity. This is preferable with the feedback resistors 30 and 31 as well. As described earlier, transistors 145, 146 can be area scaled devices which, together with the selection of the resistances of resistors 150 and 151, can provide an offset corresponding to the offset between the junctions 84, 85 and junction 93. The use of current sources or sinks stabilizes the currents over the voltage ranges of interest.

Reversion Circuit 22 functions as the interference discriminator in a manner similar to the circuit disclosed in the aforementioned U.S. Pat. No. 3,927,677. The signal received from the Buffer 22 is amplified, inverted and appears at the terminal 111 which is coupled through contact G to the second level capacitor 128 and through the high impedance resistor 131 to the reference level capacitor 125. A further resistor 127 is coupled between the terminal 126 (coupled to line G and to the terminal 111) on a positive side of the capacitor 128 and to the sensitivity control transistor collectors of transistors 152-155. The capacitor 125 is coupled through the resistor 131 and to the base of transistor 130, whereas the capacitor 128 is similarly coupled through resistor 127 to the base of transistor 129. Transistors 129, 130, 145 (operating as a diode) and 146 and resistors 150 and 151 are coupled between source voltage and ground and to the respective capacitors 128 and 125 to operate as a differential amplifier. The collector of transistor 130 is coupled to the base of transistor 147 which is coupled at its collector through resistor 149 to source voltage $+V$ and at its emitter to the emitter of transistor 155 and the base of output transistor 162. When transistor 147 is rendered conductive, it applies current to the emitter of transistor 155 to render it nonconductive and to the base of transistor 162 to render it conductive to produce an output signal at the terminal 163 in the manner hereinbefore described.

To summarize the operation of the circuit as previously described, the incoming signal at terminals 111, 126 is integrated by the instantaneous level integrator comprising the capacitor 128 which develops a voltage that is reflected through resistor 127 to the base of the differential transistor 129. The signal is concurrently applied to the reference level integrator comprising the resistor 131 and capacitor 125. The higher R-C time constant of the reference level integrator causes capacitor 125 to charge more slowly than capacitor 128. In the absence of any continuous EMI, the instantaneous level capacitor 128 and reference level capacitor 125 will draw unequal charging currents which will be reflected to the base terminals of the respective differential transistors 129 and 130. Both transistors 129 and 130 will tend to conduct, albeit unequally, but sufficiently to allow source current to be applied to transistor 130 to the base of transistor 147 to thereby render it conductive and produce an output signal in the manner hereinbefore described. Upon the termination of the signal at terminal 111, 126 (in the absence of continuous EMI), the capacitors 128 and 125 will discharge to approximately $+Vcc/2$.

In the presence of continuous EMI, the initial transition of the signal at terminal 111, 126 if sufficiently high, may be interpreted erroneously as a natural heart signal in the manner described above. However, the continuous signal will soon cause the reference level integrator and the instantaneous level integrator to achieve substantially equivalent voltage levels, and the differential transistors 129 and 130 will cease to respond to produce output signals. Should an R wave or a P wave (depending on the application of the sense amplifier) be amplified and applied to the terminal 111, 126, it will represent a higher voltage excursion than the prevailing integrated levels on the capacitors 128 and 125. The signal will thus commence to charge the instantaneous level integrator capacitor 128 at a rate exceeding the rate of charge of the reference level integrator capacitor 125, and the differential circuit will respond to the differing rates of integration of the incoming signal to produce an output signal in the manner described above, despite the presence of the continuing EMI. The operation of the circuit just described is equivalent to the operation of the circuit disclosed in the aforementioned U.S. Pat. No. 3,927,677 and my earlier U.S. Pat. No. 4,266,551. The principal distinction between the circuit depicted in FIGS. 1A and 1B from my earlier U.S. Pat. No. 4,266,551 in the elimination of the blanking circuitry component depicted therein and the substitution of the Blanking Circuit depicted herein in FIG. 2.

When the circuit of FIGS. 1A and 1B is employed as a ventricular sense amplifier in the circuit of U.S. Ser. No. 235,069, and during the initial 8-15 ms of the ventricular blanking interval, the inputs 35 and 36 are also disconnected from the ventricular terminals of the pulse generator which are adapted to be connected to the patient's heart through suitable electrode bearing leads. Preferably, FET switches are employed which are turned on and off by an appropriately timed BLANK signal developed by the digital portion of the pulse generator at the time that an atrial output stimulus is delivered to its atrial terminals.

Referring now to FIG. 2, there is shown the Blanking Circuit of the present invention which is intended to prevent the instantaneous level integrator capacitor 128 and reference level integrator capacitor 125 from discharging from levels achieved in the presence of continuous EMI during the blanking interval. The blanking circuit of FIG. 2 is a comparator circuit comprising first and second resistors 200 and 201 coupled commonly to the voltage source $+Vcc$ at terminal A, transistors 202, 204, 205 and 207, resistor 118 and input terminal 117 for receiving the BLANK signal from the digital circuitry or the control circuitry not herein illustrated. The emitter of transistor 202 is coupled to one terminal of resistor 200 and the collector of transistor 202 is coupled to the collector of transistor 207. The transistor 204 is connected as to function as a diode having its emitter coupled to the resistor 201 and its collector to the base of transistor 202 and the collector of transistor 205. The emitters of transistors 205 and 207 are together coupled to the collector of transistor 206, and the emitter of transistor 206 is coupled through the resistor 118 to receive the blanking signal at terminal 117. The base of transistor 207 is coupled to the terminal G of FIGS. 1A and 1B and to the capacitor 128. The base of transistor 205 is coupled to the terminal F of FIGS. 1A and 1B and from there to the capacitor 125. The common collector junction of transistors 202 and 207 is coupled to the terminal 112 of FIG. 1A. The base of transistor 206 is coupled to the terminal H of FIGS. 1A and 1B which is coupled to Box 41A which provides a supply-independent reference or biasing current to the base of transistor 206.

In operation, the Blanking Circuit of FIG. 2 is quiescent and draws no current and has no effect on the remaining components of the circuit depicted in FIGS. 1A and 1B as described hereinbefore. This is accomplished by coupling the blanking terminal to source voltage at terminal 117, which reverse biases the base emitter junction of transistor 206. However, when a blanking interval occurs, a ground or logic 0 voltage is applied to the BLANK input terminal 117 to forward bias the transistor 206 which is rendered conductive as long as the bias voltage at terminal H exceeds the voltage of the BLANK signal. Either the transistor 207 or the transistor 205 will be rendered conductive depending on whether the voltage on the capacitors 125 and 128 differ from one another. If the voltage on capacitor 128 exceeds that on capacitor 125, then transistor 207 would be rendered conductive to draw current from the terminal 112 coupled to the bias current source Box 41B. If, however, the charge on the capacitor 125 exceeds that of capacitor 128, the transistor 205 is rendered conductive until the charges are equalized.

The transistors 202, 204 and resistors 200, 201 constitute an active load which increases the gain, and the transistors 205, 207 are the input differential pair. If the base (line F) of transistor 205 is higher than the base (line G) of transistor 207, then the current delivered by transistor 206 is directed through the diode connected transistor 204. If the base (line G) of transistor 207 is higher than the base (line F) of transistor 205, then the current delivered by transistor 206 is directed through the transistor 202.

As stated earlier, the voltages on capacitors 125 and 128, in the quiescent condition (i.e., no EMI and no signal input), are approximately +Vcc/2, and this level is maintained by the constant current source comprising transistors 114, 115. In the presence of EMI, the average level may increase to a level exceeding +Vcc/2. In either case, it is desirable to maintain the voltage levels achieved prior to blanking on capacitors 125 and 128 relatively constant over the blanking interval. In addition, when the sense amplifier is coupled by the terminals 36, 37 to the pacemaker leads, the circuit is vulnerable to artifacts or noise which may charge capacitor 128 in the manner described. At the end of the blanking interval, the heightened charge may be mistaken as a positive sense signal and therefore it is also desirable to prevent such charging and to retain the voltage levels relatively constant.

In the absence of any such disturbing input signal, the voltage on capacitor 128 discharges very slowly through resistor 131 and tends to equalize with or fall below the voltage on reference capacitor 125. The circuit of FIG. 2 acts as a current source to the junction 112 to reverse the conductivity of buffer transistor 114, which then sources additional current to recharge instantaneous level capacitor 128 to keep the voltage relatively equal.

But in the presence of a disturbing signal at junction 93, during the blanking interval, the voltage at junction 111 rises and transistor 207 is rendered conductive. The conduction of transistor 207 draws current from junction 112 as well as the transistor 202. The current drawn from junction 112 of the constant current source renders transistor 114 less conductive and thereby slows the rate of charge of capacitor 128. Thus, the input signal is immediately drawn down by the comparator circuit of FIG. 2 and the voltage levels on the reference and instantaneous level capacitors 125 and 128 remain close to their levels preceding the disturbing signal.

In summary, a sense amplifier circuit for body tissue stimulator that discriminates useful signal from EMI during and following blanking has been described. Detection of heart (or body tissue) signals is made easier after the blanking period despite the initial transient impulse of the noise signal.

Although the new circuit has been described in the context of a digital control pacemaker timing circuit, it will be recognized that it can as well be utilized in heart pacemakers of any of the known types, analog or digital, that employ sense amplifiers whether synchronous, demand, atrial or ventricular or combinations thereof. In addition, circuit may be advantageously employed in body tissue stimulators of other types, e.g. nerve or deep brain stimulators. It is therefore to be understood that, within the scope of the appended claims, the invention may be practiced otherwise than as specifically described.

I claim:

1. A cardiac signal amplifier of the type having terminal means for receiving input signals, output means for providing an output signal upon detection of natural heart signal and blanking signal receiving means for blanking the signal amplifier for a predetermined blanking time interval, comprising:

reference level integrating circuit means for establishing a reference level signal representative of sensed extraneous repetitive noise input signals received from said terminal means;

instantaneous level integrating circuit means for establishing an instantaneous level signal representative of non-recurring signals received from said terminal means;

means responsive to said reference level and instantaneous level signals for providing said output signal when said instantaneous level signal exceeds said reference level signal by a predetermined signal level;

current supply means for establishing a predetermined minimum signal level on said reference level and instantaneous level integrating circuits in the absence of any signal inputs on said terminal means and for establishing said reference and instantaneous signal levels on said integrating circuits in the presence of noise and heart signals; and comparator means having a first input coupled to said reference level integrating circuit means and a second input coupled to said instantaneous level integrating circuit means and an output coupled to said current supply means and operative during blanking of said signal amplifier for maintaining said instantaneous signal level nearly equal to said reference signal level during blanking of said sense amplifier.

2. The signal amplifier of claim 1 wherein said current supply means comprises unity gain buffer means which is responsive to input signals for providing charging current to said reference level and instantaneous level integrating circuits; and wherein said comparator means provides a current sink to decrease said charging current when said instantaneous signal level exceeds said reference signal level during blanking.

3. The signal amplifier of claim 2 wherein said comparator means further provides current source to increase said charging current when said instantaneous signal level falls below said reference signal level during blanking.

* * * * *

UNITED STATES PATENT AND TRADEMARK OFFICE
CERTIFICATE OF CORRECTION

PATENT NO. : 4,379,459
DATED : April 12, 1983
INVENTOR(S) : Marc T. Stein

It is certified that error appears in the above-identified patent and that said Letters Patent are hereby corrected as shown below:

Column 8,

Line 39, "and" should be --the--;

Column 10,

Line 17, after "4,266,551" insert --resides--.

Signed and Sealed this

Twenty-eighth Day of June 1983

[SEAL]

Attest:

GERALD J. MOSSINGHOFF

Attesting Officer     Commissioner of Patents and Trademarks